United States Patent [19]

Ejlersen et al.

[11] Patent Number: 4,976,701
[45] Date of Patent: Dec. 11, 1990

[54] INJECTION APPARATUS

[75] Inventors: Henning M. Ejlersen, Vedbaek; Flemming Tullin, Ballerup, both of Denmark

[73] Assignee: Nordisk Gentofte A/S, Gentofte, Denmark

[21] Appl. No.: 241,973

[22] Filed: Sep. 8, 1988

[30] Foreign Application Priority Data

Sep. 25, 1987 [DK] Denmark ............................ 5045/87

[51] Int. Cl.$^5$ .............................................. A61M 5/32
[52] U.S. Cl. ................... 604/192; 604/187; 604/198; 604/200; 604/201; 206/365
[58] Field of Search ............... 604/187, 181, 192, 198, 604/200, 201, 188, 206; 206/364–366

[56] References Cited

U.S. PATENT DOCUMENTS

| | | | |
|---|---|---|---|
| 3,825,003 | 7/1974 | Kruck | 206/365 X |
| 3,967,621 | 7/1976 | Schwarz . | |
| 4,009,716 | 3/1977 | Cohen | 604/192 |
| 4,303,069 | 12/1981 | Cohen | 604/192 X |
| 4,731,059 | 3/1988 | Wanderer et al. | 604/192 |

FOREIGN PATENT DOCUMENTS

| | | |
|---|---|---|
| 1551012 | 8/1966 | France . |
| 1183100 | 3/1970 | United Kingdom . |

*Primary Examiner*—Richard J. Apley
*Assistant Examiner*—Jennifer L. Doyle
*Attorney, Agent, or Firm*—Ladas & Parry

[57] ABSTRACT

An injection apparatus has a jacket having a front end and a cartridge for containing a liquid having a rubber membrane closing a front end of the cartridge at the front end of the jacket. A double-ended needle is held in a needle holder such that both ends thereof are exposed and oriented, one end at the membrane for piercing the membrane to obtain the liquid from the cartridge, and the opposite end for injecting the liquid. First cooperative threads on a cap and the jacket are for screwing the cap onto the jacket and unscrewing the cap therefrom, the first cooperative threads having a first pitch and a first rotational hand. Second cooperative threads are on the needle holder and one of the cap and cartridge, the second cooperative threads having a second pitch and a second rotational hand, which is opposite of the first rotational hand, for moving the needle holder and needle axially upon relative rotation between the cap and cartridge, whereby the one end of the needle pierces the membrane when the cap is unscrewed. A protective case is slidable in the cap axially for protecting the opposite end of the needle at least when the cap is screwed onto the jacket and while the cap is being unscrewed therefrom. A compression coil spring in the cap biases the protective case towards the needle holder at least while the cap is being unscrewed from the jacket.

20 Claims, 3 Drawing Sheets

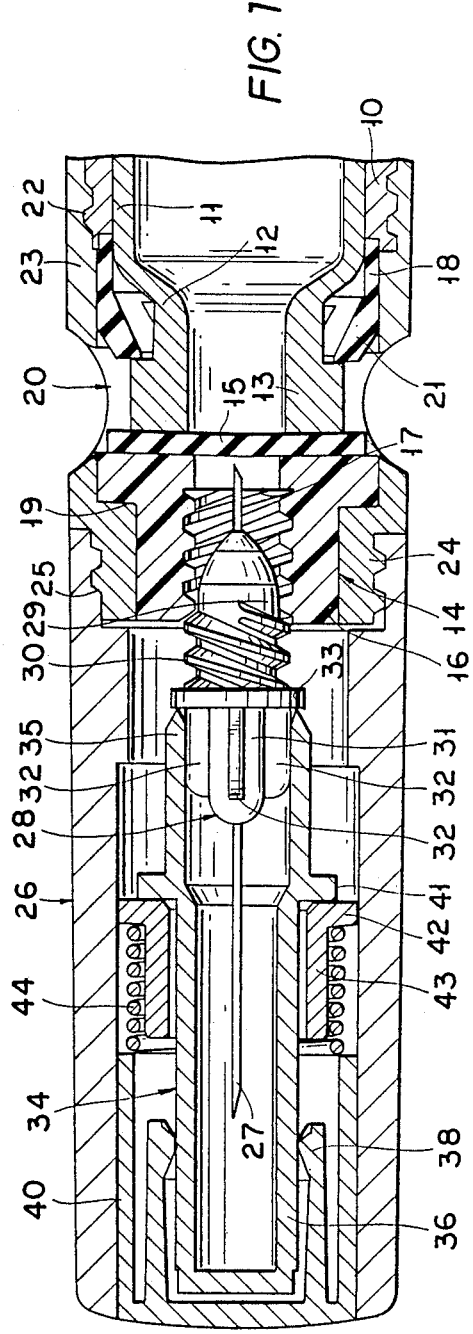
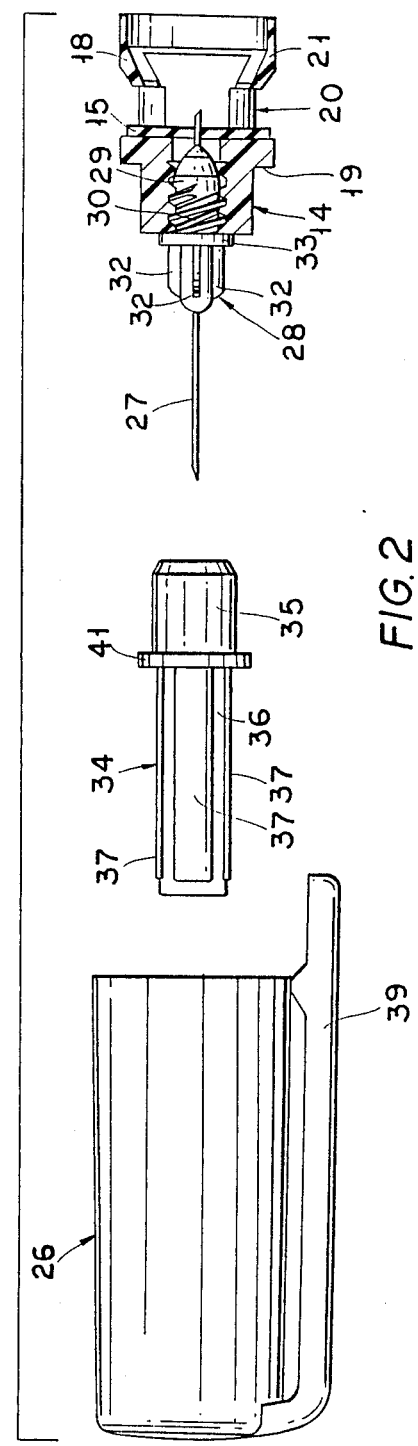
FIG. 1
FIG. 2

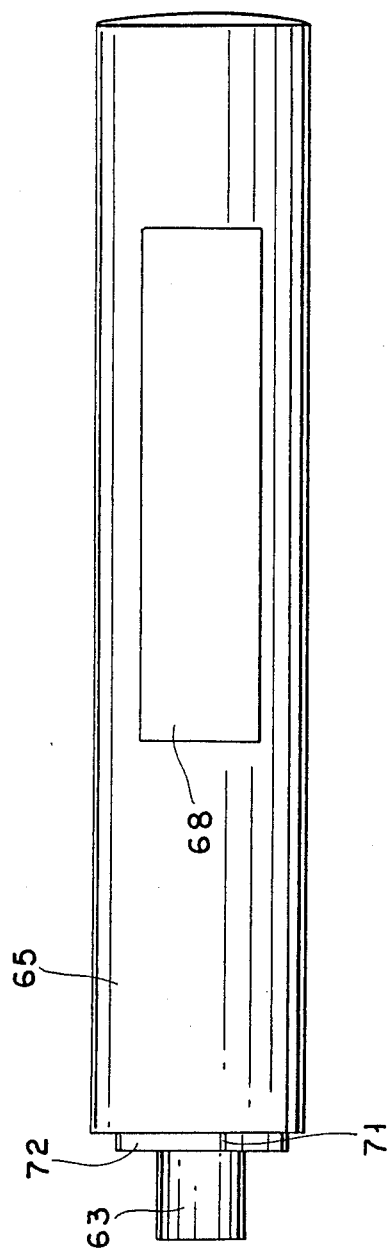

INJECTION APPARATUS

The invention concerns an injection apparatus having a cylindrical jacket to receive a cartridge, and a cap which can be applied and removed by screwing movement, as well as a double-ended needle in a needle holder which can be so connected with a cartridge, inserted in the cap, by screwing movement that one end of the needle penetrates the rubber membrane of the cartridge in one end position of the needle holder, the threads causing the two screwing movements being so shaped and arranged with respect to each other that a needle positioned in said end position is pulled out of the cartridge rubber membrane of the cartridge by application of the cap.

Since the needle is pulled out of the cartridge when the cap is screwed on, the rubber membrane of the cartridge will close so that no carrier liquid or insulin molecules leak out, e.g. because of temperature fluctuations when the apparatus is not used. Such leakage might change the concentration of insulin in the residual contents of the cartridge.

The object of the invention is to provide an injection apparatus of the present type in which the needle is effectively protected against pollution and unintentional touch, except in the actual state of use.

This object is achieved in one embodiment in that a protective case for the free end of the needle is slidably arranged in the cap and affected by a compression screw spring in the cap to engage the needle holder. The compression screw spring also ensures that the needle holder, following re-application of the cap, remains in position for re-insertion of the needle into the cartridge when the cap is screwed off again.

In another preferred embodiment of the invention, the needle holder is adapted to be mounted slidably, but fixed against rotation on the cartridge and has external threads for cooperation with internal threads in the cap, said threads having a considerably greater pitch than the screwing-on threads of the cap, said protective case being adapted to be placed as a slight friction fit in an axially movable and spring loaded case holder contained in the cap. The advantage is that the two sets of threads have the same conventional screwing-on and screwing-off directions, and that the protective case remains in the cap when this is screwed off so that the user has only two parts to handle.

The invention will be explained more fully below with reference to the drawing, in which:

FIG. 1 is a longitudinal cross section through one, cap-end portion of one embodiment of an injection apparatus according to the invention;

FIG. 2 is an exploded view of most of the cap-end portion of the injection apparatus of FIG. 1, partly in longitudinal cross section, rotated 90°, and on a slightly smaller scale;

FIG. 5 is a side view of the cap shown in FIG. 3, but turned 90° therefrom.

Figure 3:
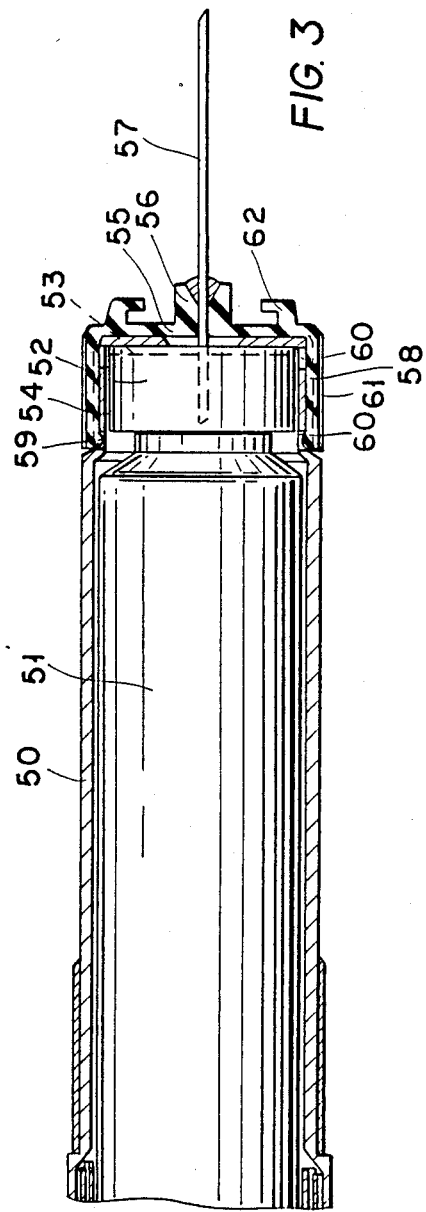
FIG. 3 is a side view, partly in longitudinal cross section, of one, cap end of a jacket portion of another embodiment of an injection apparatus according to the invention without the cap.

In FIG. 1, one end of a jacket 10 accommodates a cartridge consisting of a cylindrical glass case 11, which has a neck 12 and a collar 13 successively at the one end, a plastics sleeve at 14, and a rubber membrane 15 therebetween. The plastics sleeve has a front part 16 formed with internal right-handed threads 17, and a rear, cylindrical part 18 surrounding the front part of the glass case 11. A ring-shaped shoulder 19 is provided between the two parts 16 and 18. The rear part 18 is formed with openings at 20 which are disposed opposite each other and which adjoin the front part 16, and with two elastically resilient fins 21 extending from the rear edge of each opening obliquely inwardly to engage the rear side of the neck 13 of the glass case.

The cartridge 11, 14, 15 is secured in the injection apparatus by means of a sleeve-shaped intermediate member consisting of a rear part 23 formed with internal right-handed threads 22 and screwed on the jacket 10, and of a front part 24 having a slightly smaller diameter and external left-handed threads 25 on which a cap at 26 is threaded. Between the two parts 23 and 24, the intermediate member has an internal ring-shaped shoulder face which engages the shoulder 19 of the plastics sleeve at 14. The front intermediate member part 24 tightly surrounds the front plastics sleeve part 16. The two mating faces have a shape different from cylinder shape so that the two parts are fixed against rotation with respect to each other. The rear intermediate member part 23 is formed with two openings disposed opposite their respective openings 20 in the plastics sleeve at 14.

A needle 27, which is pointed at both of its opposite, front and rear ends, is passed through a needle holder at 28 consisting of plastics. The needle holder has a rear, shell-shaped part 29 with right-handed threads 30 that are rotatable with the threads 17 of the plastics sleeve at 14, a front, cylindrical part 31 having four external orthogonal radial fins 32 (only three shown) and an intermediate flange 33 between the front and rear parts. When the needle holder is screwed into the plastics sleeve of the cartridge, as shown in FIG. 2, the rear end of the needle penetrates through the rubber membrane 15, whereby the contents of the cartridge, e.g. a carrier liquid and suspended insulin particles, can be pressed out through the needle by activation of a piston (not shown) in the glass case 11 for use.

When the needle is not in use, its front part is surrounded by a protective case at 34. The rear part 35 of the protective case at 34 frictionally grips the fins 32 of the needle holder 28 and is internally formed with a narrow, low rib (not shown) which protrudes between two of these fins. The front part 36 of the protective case is externally formed with longitudinal, low ribs 37 (FIG. 2) and is surrounded by a plurality of resilient fingers 38 (FIG. 1). The fingers extend from the bottom of an end member 40, which is formed with a clip 39 (FIG. 2) and pres-fit in the frontmost end of the cap 26. Between its two parts 35 and 36, the protective case 34 has an annular flange 41 against which a flange 42 on a sleeve-shaped insert 43 is kept engaged by one end of a compression coil spring 44 that surrounds the insert, the opposite end of the spring engaging the end member 40.

When the cap 26 is screwed onto the injection apparatus, to the position shown in FIG. 1, the needle holder at 28 does not screw into the sleeve at 14 owing to the opposite direction of the threads 17 and 25 and the needle 27 thus stays withdrawn from the rubber membrane 15, which continues to seal the contents of the cartridge, therefore. When the cap 26 is screwed off, however, the protective case 34 follows the relative rotary movement of the cap and carries along the needle holder 28, which, owing to the oppositely directed threads, is thus screwed into the plastics sleeve 14 of the cartridge, whereby the needle 27 pierces the rubber membrane 15, as described above and shown in FIG. 2. After axial removal of the protective case 34 thereafter, the injection apparatus is ready for use.

After use, the protective case is applied again, and the cap is screwed on, so that the co-rotating protective case screws the needle holder 28 back to the position shown in FIG. 1 against the effect of the spring 44. In this position, the rubber membrane 15 closes the hold left by the needle, so that, irrespective of possible temperature fluctuations, neither carrier liquid nor insulin particles can leak out of the cartridge. Meanwhile, the spring 44 resiliently holds the needle holder in the proper position for renewed threading into the cartridge.

Figure 4:
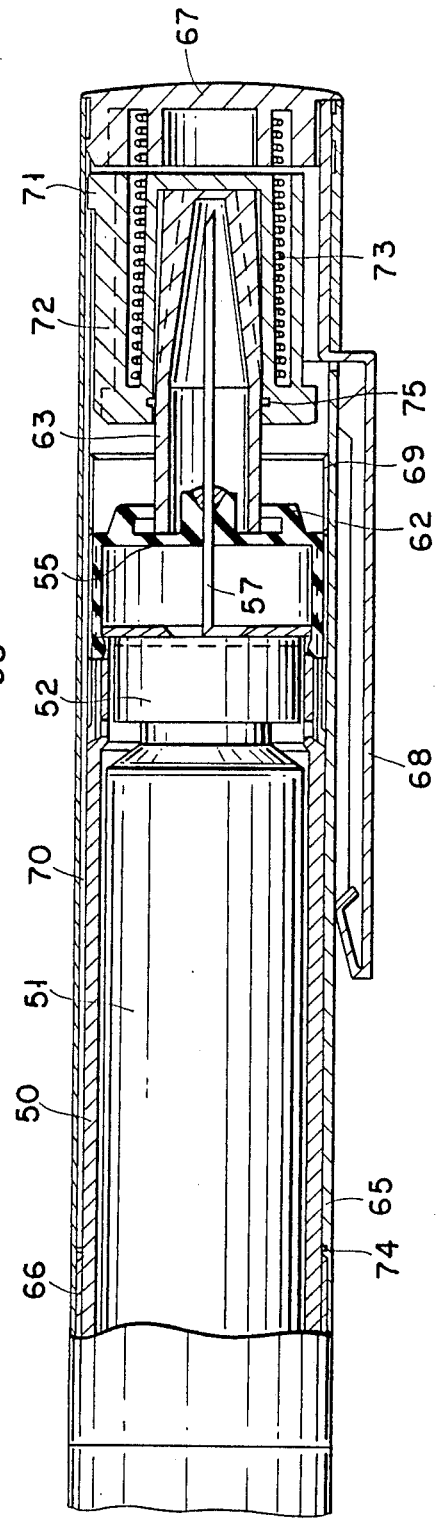
FIG. 4 is a side view, partly in longitudinal cross section, of the embodiment shown in FIG. 3 in another position, and with the cap.

In the embodiment shown in FIGS. 3-5 a reduced-diameter cap-end part 54 of a jacket 50 shown in FIGS. 3 and 4 accommodates a beaded metal collar 52, which secures a rubber membrane 53. On the outside of the reduced-diameter end part 54 of the jacket 50 there is slidably mounted a bowl-shaped needle holder 55 made from an elastic plastics material and having a hub 56 through which a needle 57 is passed. The cylindrical wall of the needle holder is formed with two fingers 58 which are disposed diametrically opposite each other. Each finger has its outer end an inwardly directed, hemispherical boss 59 which can slide in a corresponding axial groove in the jacket part 54 between holes 60 that receive the boss 59 at opposite ends of the groove. On the outer side, the cylindrical part of the needle holder has threads 61 of great pitch. The bottom of the needle holder is formed with a ring-shaped protrusion 62 having an angular cross-section. This protrusion forms a well to receive the inner end of a protective case 63 for the outer end of the needle 57.

The cap 65 of the injection apparatus is threaded on the jacket 50 by threads 66 at the open end of the cap. A clip 68 is secured in an end member 67 of the cap. The inner side of the cap is formed with threads 69 for co-operation with threads 61 of the needle holder 55 and with three axial grooves 70 to receive guide fins 71 on a needle case holder 72 which is slidably movable in the cap. This holder forms a cylindrical well to receive the outer end of a protective case 63 for the needle and is under the action of a compression coil spring 73 which is embedded in ring-shaped tracks in the holder and the end member 67.

When the cap is removed as shown in FIG. 5, the movement of the holder 72 in an outward direction is limited by the engagement of the guide fins with a spring ring 74, which is embedded in the cap at the inner end of the threads 66. Another spring ring 75, which is embedded in the outer end of the needle case holder 72, serves to grip the case 63 with such friction that the case remains in the cap when the cap is removed.

When the cap 65 is screwed on the jacket 50 with the cartridge 51 positioned in it, the threads 69 engage the threads 61 of the needle holder 55. The screwing-on threads 66 have a relatively great pitch, but the needle holder threads 61 and the corresponding cap threads 69 have a so much greater pitch and are so positioned in the cap that when the cap is screwed on, the needle holder 55 is pulled from the position shown in FIG. 3 in which the needle 57 extends through the rubber membrane 53 of the cartridge, to the position shown in FIG. 4 in which the needle is pulled out of the membrane. It is noted in this connection that the engagement of the bosses 59 with the grooves of the jacket end part 54 prevents the needle holder from rotating with respect to the jacket.

When the cap is applied, first the needle protective case 63 accommodated in it is passed inwardly over the exposed needle and into the well formed by the needle holder protrusion 62, and during the continued application movement the case holder 72 is urged backwards against the effect of the spring 73.

When the cap is screwed off, the two threads 61 and 69 move the needle holder back to the position shown in FIG. 3, in which the inner end of the needle is present in the liquid contained in the cartridge.

We claim:

1. In an injection apparatus having a cylindrical jacket to receive a cartridge having a membrane, and a cap having internal threads for cooperation with external threads on said jacket, as well as a double ended needle placed in a needle holder which is provided with external threads for cooperation with internal threads in the cartridge so that axial movement of the needle holder produced by screwing said holder into said cartridge causes one, end of the needle to penetrate the membrane of the cartridge in one end position of the needle holder, the external and internal threads being so shaped and arranged with respect to each other that the one end of the needle thereafter is pulled out of the membrane by application of the cap, the improvement in that a protective case for the opposite end of the needle is slidably arranged in the cap, and that a compression coil spring is so mounted in the cap between a fixed portion thereof and a portion of the protective case as to urge the latter from a retracted position towards the needle holder.

2. An injection apparatus according to claim 1, in which the needle holder has a rear part with the external threads for cooperation with the internal threads in the cartridge, said threads being directed oppositely to the screwing-on threads of the cap, characterized in that the needle holder moreover has a front part which is adapted to contact the protective case in such a manner that said case can be slidably moved, but can at most be rotated through a limited angle with respect to the needle holder.

3. An injection apparatus according to claim 2, characterized in that a rear part of the protective case is formed with longitudinal, low ridges, and that a plurality of resilient fingers extends from the bottom of the cap, said fingers surrounding the rear part of the protective case when said case is in the retracted position.

4. In an injection apparatus having a cylindrical jacket to receive a cartridge having a membrane, and a cap having first internal threads for cooperation with external threads on said jacket, as well as a double ended needle placed in a needle holder mounted slidably, but fixed against rotation, on the cartridge, and having external threads for cooperation with second internal threads in the cap, said second threads having a considerably greater pitch than said first internal threads in the cap so that axial movement of the needle holder produced by screwing said holder into said cartridge causes one end of the needle to penetrate the membrane of the cartridge in one end position of the needle holder, the external and internal threads being so shaped and arranged with respect to each other that the one end of the needle thereafter is pulled out of the membrane by application of the cap, the improvement in that a protective case for the opposite end of the needle is slidably arranged in the cap, and that a compression coil spring is so mounted in the cap between a fixed portion thereof an da portion of the protective case as to urge the latter from a retracted position towards the needle holder.

5. An injection apparatus, comprising:
a jacket having a front end;
a cartridge for containing a liquid, the cartridge being in the jacket and having a rubber membrane closing a front end of the cartridge at the front end of the jacket;
a needle having an axis and a needle holder, the needle being pointed at one end and at an axially opposite end, and the needle holder being at the front ends of the jacket and cartridge and holding the needle such a that both of the one and opposite ends thereof are exposed and oriented, the one end at the membrane for piercing the membrane, whereby to obtain the liquid from the cartridge, and the opposite end for injecting the liquid;
a cap for covering the front ends of the jacket and cartridge and for covering the needle and needle holder;
first cooperative thread means on the cap and the jacket for screwing cap onto the one of the jacket and cartridge and unscrewing the cap therefrom, the first cooperative thread means having a first pitch and a first rotational hand for the screwing;
second cooperative thread means on the needle holder and one of the cap and cartridge, the second cooperative thread means having a second pitch and a second rotational hand for screwing, the second rotational hand being the opposite of the first rotational hand for moving the needle holder and needle axially of the needle upon relative rotation between the cap and cartridge, whereby the one end of the needle pierces the membrane when the cap is unscrewed;
a protective case slidable in the cap axially of the needle for protecting the opposite end of the needle at least when the cap is screwed onto the jacket and while the cap is being unscrewed therefrom; and
a compression coil spring means in the cap and resiliently operative between the cap and protective case for sliding the protective case towards the needle holder at least while the cap is being unscrewed from the jacket.

6. The injection apparatus according to claim 5, wherein the second cooperative thread means comprises external threads on a rear part of the needle holder a that is at the front end of the cartridge, internal threads on the front end of the cartridge for cooperation with the external threads, and first rotating means on a front part of the protective case at the needle holder and a front part of the needle holder at an end of the needle holder opposite the rear part of the needle holder cooperative for rotating the needle holder with the protective case while permitting sliding movement therebetween in the directions of the axis of the needle.

7. The injection apparatus according to claim 6, wherein the first rotating means comprises at least one fin on the needle holder at least generally parallel to the needle axis and at least one rib on the protective case for engagement with the fin upon rotation of the protective cap relative to the needle holder.

8. The injection apparatus according to claim 6, wherein the second cooperative thread means further comprises second rotating means on the cap and protective case cooperative for rotating the same together and permitting relative sliding movement therebetween in the directions of the axis of the needle.

9. THe injection apparatus according to claim 7, wherein the second cooperative thread means further comprises second rotating means on the cap and protective case cooperative for rotating the same together and permitting relative sliding movement therebetween in the direction of the axis of the needle.

10. The injection apparatus according to claim 8, wherein the second rotating means comprises at least one rib on the protective case at least generally parallel to the axis of the needle and at least one finger on he cap for engagement with the rib upon rotation of the cap relative to the protective case.

11. The injection apparatus according to claim 9, wherein the second rotating means comprises at least one rib on the protective case at least generally parallel to the axis of the needle and at least one finger on the cap for engagement with the rib upon rotation of the cap relative to the protective case.

12. The injection apparatus according to claim 5,
wherein the second cooperative thread means comprises internal threads on the cap, external threads on the needle holder for cooperation with the internal threads, and sliding means on the needle holder and one of the cartridge and jacket for preventing relative rotation between the needle holder and the one of the cartridge and jacket while permitting relative sliding therebetween, and
further comprising retaining means in the cap for retaining the protective case in the cap when the cap is unscrewed from the jacket and spaced therefrom.

13. The injection apparatus of claim 5, wherein the second pitch is greater than the first pitch.

14. The injection apparatus of claim 6, wherein the second pitch is greater than the first pitch.

15. The injection apparatus of claim 7, wherein the second pitch is greater than the first pitch.

16. The injection apparatus of claim 8, wherein the second pitch is greater than the first pitch.

17. The injection apparatus of claim 9, wherein the second pitch is greater than the first pitch.

18. The injection apparatus of claim 10, wherein the second pitch is greater than the first pitch.

19. The injection apparatus of claim 11, wherein the second pitch is greater than the first pitch.

20. The injection apparatus of claim 12, wherein the second pitch is greater than the first pitch.

* * * * *